(12) United States Patent
Benzie et al.

(10) Patent No.: US 6,177,260 B1
(45) Date of Patent: Jan. 23, 2001

(54) MEASUREMENT OF ANTIOXIDANT (REDUCING) POWER AND/OR ANTIOXIDANT CONCENTRATION

(75) Inventors: Iris F. F. Benzie, Kowloon (HK); John Joseph Strain, Port Stewart (GB)

(73) Assignee: The Hong Kong Polytechnic University, Kowloon (HK)

(*) Notice: Under 35 U.S.C. 154(b), the term of this patent shall be extended for 0 days.

(21) Appl. No.: 08/893,519

(22) Filed: Jul. 11, 1997

(51) Int. Cl.⁷ .............................. C12Q 1/26; C12Q 1/28; G01N 33/48; G01N 21/75
(52) U.S. Cl. .............................. 435/25; 435/28; 436/63; 436/164
(58) Field of Search .............................. 435/25, 27, 28, 435/190, 191, 810; 436/93, 20, 43, 63, 71, 99, 161, 162, 164, 808, 815

(56) References Cited

U.S. PATENT DOCUMENTS

| | | | |
|---|---|---|---|
| 3,711,252 | * 1/1973 | Roy | 422/56 |
| 4,247,471 | * 1/1981 | Klein et al. | 554/169 |
| 4,806,415 | * 2/1989 | Fossati | 435/14 |
| 5,395,755 | * 3/1995 | Thorpe et al. | 435/28 |
| 5,427,951 | * 6/1995 | Davies et al. | 436/66 |
| 5,763,281 | * 6/1998 | Weisheit et al. | 436/74 |

FOREIGN PATENT DOCUMENTS

| | | |
|---|---|---|
| 2245062 | 3/1994 | (GB). |
| 54134694 | * 4/1978 | (JP). |

OTHER PUBLICATIONS

Lewin et al., "Photochemiluminescent Detection of Antiradical Activity; III: A Simple Assay of Ascorbate in Blood Plasma", J. Biochem. Biophys. Methods 28, 1994, pp. 277–282.

Pachla et al., "Analytical Methods for Determining Ascorbic Acid in Biological Samples, Food Products, and Pharmaceuticals", J. Assoc. Off. Anal. Chem., vol. 68, No. 1, 1985, pp. 1–12.

Popov et al., "Photochemiluminescent Detection of Antiradical Activity: II. Testing of Nonenzymic Water–Soluble Antioxidants", Free Radical Biology and Medicine, vol. 17, No. 3, 1994, pp. 267–271.

Gey et al., "Increased risk of Cardiovascular Disease at Suboptimal Plasma Concentrations of Essential Antioxidants: an Epidemiological Update With Special Attention to Carotene and Vitamin $C^{1-3}$", Am. J. Clin, Nutr. 57 (Suppl.), 1993, pp. 787S–797S.

John M.C. Gutteridge, "Biological Origin of Free Radicals, and Mechanisms of Antioxidant Protection", Chemico–Biological Interactions, 91 (1994), pp. 133–140.

Steinberg et al., "Antioxidants in Prevention of Human Atherosclerosis", NHLBI Workshop, Sep. 5–6, 1991, pp. 2338–2344.

K. F. Gey, "Prospects for the Prevention of Free Radical Disease, Regarding Cancer and Cardiovascular Disease", British Medical Bulletin, vol. 49, No. 3, 1993, pp. 679–699.

Wayner et al., "The Relative Contributions of Vitamin E, Urate, Ascorbate and Proteins to the Total Peroxyl Radical–Trapping Radical–Trapping Antioxidant Activity of Human Blood Plasma," Biochimico et Biophysica Acta, 924, 1987, pp. 408–419.

Iris F. F. Benzie., "An Automated, Specific, Spectrophotometric Method for Measuring Ascorbic Acid in Plasma (EFTSA)", Clinical Biochemistry, vol. 29, No. 2, 1996, pp. 111–116.

Benzie et al., The Ferric Reducing Ability of Plasma (FRAP) as a Measure of "Antioxidant Power": The FRAP Assay, Analytical Biochemistry, 239, 1996, pp. 70–76.

Liu et al., "Specific Spectrophotometry of Ascorbic Acid in Serum or Plasma by Use of Ascorbate Oxidase", Clinical Chemistry, vol. 28, No. 11, 1982, pp. 2225–2228.

Lissi et al., "Evaluation of Total Antioxidant Potential (Trap) And Total Antioxidant Reactivity From Luminol–Enhanced Chemiluminescence Measurements", Free Radical Biology & Medicine, vol. 18, No. 2, 1995, pp. 153–158.

Miller et al., "Spectrophotometric Determination of Antioxidant Activity", Redox Report, 2(3), 1996, pp. 161–171.

Whitehead et al., "Enhanced Chemiluminescent Assay for Antioxidant Capacity in Biological Fluids", Analytica Chimica Acta, 266, 1992, pp. 265–277.

(List continued on next page.)

\* cited by examiner

Primary Examiner—Jon P. Weber
(74) Attorney, Agent, or Firm—Leydig, Voit & Mayer, Ltd.

(57) ABSTRACT

A method for measuring the antioxidant capacity and/or the amount of a specific antioxidant in a sample, which comprises:

a) at least two samples (A) and (B) to be assayed in parallel;
  b) addition of an antioxidant deactivator to sample (A) which selectively deactivates the antioxidant ability of an antioxidant in the sample;
  c) addition of a redox indicator to both samples (A) and (B), the indicator being capable of indicating the antioxidant capacity of each sample absorbance of electromagnetic radiation;
  d) measurement of the change in absorbance of electromagnetic radiation of the indicator in each sample at a given time interval, from the time when the redox indicator was added to or mixed with the samples or immediately prior to this addition or mixing until a given time after the redox indicator was added;
  e) determining the antioxidant capacity of the sample and/or the specific antioxidant in the sample, by relating the change in absorbance of electromagnetic radiation of step (d) to the absorbance value of a standard solution run under the same conditions or to molar absorptivity value.

12 Claims, 7 Drawing Sheets

OTHER PUBLICATIONS

John M. C. Gutteridge, "Lipid Peroxidation and Antioxidants as Biomarkers of Tissue Damage" Clinical Chemistry, vol. 41, No. 12, 1995, pp. 1819–1827.

Roland Stocker, "Lipoprotein Oxidation: Mechanistic Aspects, Methodological Approaches and Clinical Relevance", Current Science Ltd., 1994, pp. 422–433. vol. 5.

Jialal et al., "Low–Density Lipoprotein Oxidation, Antioxidants, and Atherosclerosis: A Clinical Biochemistry Perspective", Clinical Chemistry, vol. 42, No. 4, 1996, pp. 498–506.

Miller et al. Clin. Sci. (1993) 84: 407–12, 1993.*

Arnao et al. Analytical Biochem. (1990) 185(2): 335–8 (abstract only), Mar., 1990.*

Rice–Evans et al. Free Radical Biol. Med. (1996) 20(7): 933–56, 1996.*

Fraser, F.H., "Characterization of Metal–ligand Pi Bonding in Iron and Cobalt Complexes of Dipyridyl–s–Triazine Derivatives", Diss. Abstr. Int. B, 34(3), 1030, in Chem Abstr. AN 79:132440, 1973.*

MEASUREMENT OF ANTIOXIDANT (REDUCING) POWER AND/OR ANTIOXIDANT CONCENTRATION

FIELD OF THE INVENTION

This invention concerns a method of measuring the antioxidant (reducing) power and antioxidant concentration of a sample, in particular various biological fluids, pharmaceuticals, beverages, herbs, herbal remedies and foodstuffs.

BACKGROUND OF THE INVENTION

In the invention described, the terms "antioxidant (or reducing or reductive) capacity, antioxidant (or reducing or reductive) power, antioxidant (or reducing or reductive) ability, antioxidant (or reductive or reducing)" are held to be synonymous and interchangeable. Oxidising species, or reactive oxidant species, are known to contribute to the cause of a number human diseases. In situations or conditions where antioxidant defence is inadequate, there may be oxidative changes to DNA, protein and lipids, which may lead to various degenerative diseases, such as coronary hear disease, cancer, diabetes, arthritis and cataracts (Gey K. F., Br. Med. Bull., (1993), 49, 679–99; Steinberg D., Circulation, (1992), 85, 2338–44; Cutteridge J. M. C., (1994) 91, 133–40; Gey K. F. et al, Am. J. Clin. Nutr., (1993), 57, 787S–797S).

Measurement of antioxidant status of biological fluids and tissues may be useful in the study of pro-oxidant:antioxidant balance and the risk of, or defence against, diseases associated with oxidative damage. The relative contributions to this by individual antioxidants, and assessment of the potential for ingestion or treatment with foodstuffs, pharmaceuticals, vitamin preparations, herbs etc., to improve antioxidant status may be useful in helping to plan risk reduction/health promoting strategies.

The term "antioxidant," can be employed as a generic term describing a group of compounds which may prevent the generation of oxidising species, remove such species or inactivate them, thus preventing, delaying or minimising oxidative changes to important biomolecules. Members of this group are diverse in structure and action, and include metal chelating compounds and enzymes such as catalase and superoxide dismutase. However, one important antioxidant sub-group comprises electron donating (i.e. reducing) antioxidant, such as (but not limited to) ascorbic acid (vitamin C), alpha, beta, gamma and delta tocopherols and tocotrienols (collectively known as "vitamin E"), uric acid, bilirubin, phenolic group compounds such as flavonoids, and thiol group-containing compounds such as protein and glutathione. Electron donating antioxidants, also known as scavenging and chain breaking antioxidants, destroy or inactivate oxidising species by means of electron transfer from "antioxidant" to the oxidant. In this application, the term "antioxidant" is used hereafter to describe such electron donating antioxidants.

Up until now, most tests used for measuring the antioxidant power of a sample have measured the ability of the sample to withstand the oxidative effects of reactive species purposely generated in the reaction mixture. For example, depletion of antioxidants denoted by a change in signal, such as the rate of oxygen utilisation (Wayner, D. D. M. et al, Biochim. Biophys. Acta, (1987), 924, 408–419, or chemiluminescence (GB 2245062; Popov, I. N., Free Radicals Biol. Med., (1994), 17, 267–71; Whitehead, T. P., et al, anal. Chim, Acta., (1992), 266, 265–277; Lissi, E., Free Radicals Biol. Med., (1995), 16, 581–90). However, these methods require specialised equipment and can be time consuming. Therefore, these methods are difficult to sue and limited in their applications. As a result of the lack of an inexpensive, simple, rapid and efficient method of measuring individual antioxidant and/or total antioxidant (reducing) power of biological samples, there is insufficient data on the clinical utility of assessing antioxidant status in the various disorders thought to be associated with oxidative changes/oxidative stress.

Specific antioxidants, such as ascorbic acid, are known to play a major role in antioxidant defence. However, most methods of measuring the concentration of ascorbic acid in samples are non-specific, redox linked colourimetric methods (Pachla L.A. et al, J. Assoc. Anal. Chem., (1985), 68 1–12). A more specific method has been disclosed by Liu L. S., et al, J. Chrom., (1993), 612, 63–70, which requires use of HPLC. However, this method is both time consuming and expensive. Lewin G., et al, J. Biochem. Biophys. Meth., (1994), 28, 277–82, has recently disclosed a sensitive method of measuring ascorbic acid using a photochemiluminescence method, however this method requires specialised equipment. Moreover, owing to the time consuming nature of most methods used to date, pre-treatment of samples is usually needed in order to stabilise the ascorbic acid content.

Furthermore, it is time consuming, expensive and difficult to the point of impracticality to attempt to measure all possible constituent antioxidants within a heterogeneous sample, such as blood plasma, urine, plant material, foodstuffs etc. Therefore, a method suitable for the speedy, specific and sensitive measurement of individual antioxidant (s) and/or net, overall or total antioxidant power of a wide range of sample types would have considerable advantages over currently available methods. This would especially be true if such a method could be performed on samples with no or minimal pre-treatment. Such a method would facilitate observational, clinical and nutritional studies into antioxidant defence and the role of oxidative stress in the aetiology and severity of chronic disease.

SUMMARY OF THE INVENTION

The term FRAP in the description of the invention is the ferric reducing (antioxidant) power of a sample. Also, the term FRASC is the ferric reducing antioxidant power (FRAP) and the ascorbic acid concentration of the sample, as measured by a modification of the FRAP assay in which both of these indices of antioxidant defence are measured by a single test.

It is an object of the invention to provide a simple and efficient method for measuring the antioxidant power of a sample.

It is a further, and more specific, object of the invention to provide a simple and efficient method for measuring the antioxidant power of a sample and the amount of antioxidants in a sample.

It is still a further, and more specific, object of the invention to provide a simple and efficient method for measuring the antioxidant power of a sample and the amount of a specific antioxidant in a sample.

It is still a further, and more specific, object of the invention to provide a simple and efficient method for measuring the antioxidant power of a specific antioxidant in a sample.

It is still a further, and more specific, object of the invention to provide a simple and efficient method for measuring the antioxidant power of a specific antioxidant in a sample and the amount of the specific antioxidant in a sample.

Other objects and advantages of the invention will become apparent as the description proceeds.

Redox indicators are known to undergo physiochemical change, for example a colour change, when reduced by antioxidants in a sample. This physicochemical change can be easily monitored by known methods, for example by monitoring a change in absorption, or emission, of electromagnetic radiation in a sample or by other methods that are known to monitor redox reactions. The method of the invention utilises the ability of antioxidants to reduce metal complexes to their lower oxidation state or to take part in any electron transfer reaction (i.e. a redox reaction) which causes a concomitant, direct physicochemical change in the redox partner taking the role of oxidant. For example, $Fe^{III}$-TPTZ is reduced by antioxidants to its $Fe^{II}$-TPTZ form, which is blue in colour, and hence results in an increase in absorbance at 593 nm.

the redox reaction described above is only intended to be representative of the many suitable redox reactions that may be known to those in the art. Many other known redox reactions or variations therefore are likely to be found useful for the present purposes and can be investigated by sample experimentation. The term redox indicator is sued hereafter to denote the oxidant in such redox reactions.

the amount of the redox indicator reduced by the antioxidant is a reflection of the antioxidant power of the antioxidant. Therefore, the total antioxidant power of the sample can easily be measured by recording the difference between the absorbance signal at a specific wavelength, of a reaction mixture immediately before or at the time of redox indicator/sample mixing, and the absorbance at a time after redox indicator/sample mixing. This difference in absorbance is then compared with the absorbance given by a known concentration of a standard solution at the same specific wavelength.

Similarly, the amount of antioxidants in a sample can also be determined.

The additional of an antioxidant deactivator which can selectively remove or inactivate a specific antioxidant in a sample, enables the specific antioxidant capacity of that specific antioxidant in a sample to be indirectly measured, by comparing the absorbance signal difference of the reaction mixtures with and without the antioxidant deactivator. The difference in absorbance signals between these parallel sample mixtures is due to the specific antioxidant inactivated in the sample. The specific antioxidant capacity is thus determined by comparing the difference in absorbance at a specific wavelength with the absorbance given by a known concentration of the reduced redox indicator at the same specific wavelength.

Similarly, the amount of a specific antioxidant can also be determined.

Therefore, a kit comprising a combination of these methods can be used to measure both the antioxidant capacity of an antioxidant and the concentration of a specific antioxidant in a sample.

The types of samples that can be assay by this method are wide-ranging and include biological samples, vitamin preparation, pharmaceuticals, food stuffs, beverages, water, plants, etc. Examples of biological samples which could be assayed are blood plasma or serum, urine, saliva, cerebrospinal fluid, respiratory fluid, inflammatory fluid, synovial fluid, tears, dialysate fluid, organ transport/storage/preservation fluid, etc.

The assay used in the present invention has many applications. For example, the antioxidant power of a specific antioxidant can be assessed by examining an antioxidant's ability to reduce a specific redox indicator in a sample. The assay can be used to compare batch to batch variation in antioxidant compounds, such as vitamin preparations, teas, wines, vegetable crops, etc. Also, the bioavailability of antioxidant containing substances such as drugs, medicinal preparations, foodstuffs, etc. can be assessed by measuring the antioxidant status of appropriate biological fluids before and after ingestion or treatment with the relevant substance.

The rate at which an antioxidant works can also be assessed by monitoring the time it takes to reduce a specific redox indicator. The rate at which an antioxidant works (i.e. its reaction kinetics) would be useful in characterising the antioxidants in a sample. The effect of pH, temperature, concentration and other parameters, on the effectiveness of an antioxidant can also be assessed by altering these reaction parameters and observing the antioxidant's effect on the redox indicator.

It should be noted that in the FRAP and FRASC assays described, the stoichiometric factors are constant. Therefore, if the stoichiometric factor for an individual reactant (antioxidant; reductant) is known or is measured, and/or the molar mass of this reactant is known or measured, the relative and absolute contribution of the individual reactant to the total antioxidant power of a test sample can be obtained easily.

The assay could also be used to investigage contamination, adulteration and/or storage, manufacutirng, theremal, etc. effects on substances with antioxidant properties and to investigate possible synergistic interaction between antioxidants.

Also, the effectiveness of an antioxidant deactivator to selectively remove the antioxidant capacity of a specific antioxidant can also be assessed.

The antioxidant deactivator used in the investigation can be any agent or process which is know in the art to remove an antioxidant to prevent an antioxidant from reducing the redox indicator in the reaction. Processes include dialysis, filtration or precipitation; antioxidant deactivators include enzymes which can selectively oxidise antioxidants e.g. ascorbic oxidase which can oxidise ascorbic acid, and uric oxidase which can oxidise uric acid.

The antioxidants which can be assayed by this invention are not limited and any antioxidant that is capable of reducing the redox indicator in the assay to its lower oxidation state can be used i.e. any antioxidant that has a redox potential (under the conditions used) lower than (i.e. less positive, or more negative) than the redox indicator used in the assay. For example, the measurement of the 'non-uric acid reducing power'(non-UA FRAP) in a sample, and the contribution of ascorbic acid to this, is potentially useful index of antioxidant defence. This 'non-uric acid reducing power' can be easily calculated by the additional measurement of uric acid in the sample.

High total 'antioxidant' status associated with elevated plasma uric acid concentrations may be misleading, masking a relative or absolute deficiency of other antioxidants. However, because stoichiometric factors of individual antioxidants (2.0 in the case of uric acid, ascorbic acid and alpha tocopherol, 4.0 in the case of bilirubin) are constant in the FRAP assay, and precision is high, the non-UA FRAP value can be calculated quickly and simply by subtracting twice the uric acid concentration ($\mu$mol/l) from the FRAP value ($\mu$mol/l). It is also a simple matter to calculate the relative contribution of other measured antioxidants, such as ascorbic acid, alpha tocopherol ('vitamin E') or bilirubin, to the non-UA or total FRAP.

The linearity of response in the assay is maintained over a wide range of concentrations with pure, homogeneous solutions of known antioxidants, mixtures of antioxidants in aqueous solution and heterogeneous mixtures. Also, since protein reacts poorly and slowly in the FRAP and FRASC assays, enzymes added in the quantities required to selectively destroy individual antioxidants in a sample, can be present in the reaction mixture without interfering significantly with the test results.

The time at or within which the absorbance reading is taken, after redox indicator/sample mixing, may depend on the specific antioxidant being assayed. For example it could be added that, while ascorbic acid readings should be taken within a 0–1 minute reaction time window in order to avoid interference by dehydroascorbic acid, a 0–4 minute time window is recommended for measuring the total antioxidant power of plasma or serum; the time can be modified to measure the antioxidant power of other types of samples, such as drugs, beverages or foodstuffs. For example, 0–10 minute time window may be more appropriate when comparing the measuring antioxidant power of teas.

In the present invention the assay described can be automated, for example, the Cobas Fara centrifugal analyser will enable up to 27 samples to be assayed simultaneously. It is also possible to perform the test at room temperature in a manual version, using a benchtop colourimeter and stopwatch. Various other types of automated or semi-automated instruments/analysers could also be used, e.g. random access, dry chemistry, "dip-stick" type, continuous flow, microtitre plate readers with associated precision pipetting stations/equipment. Furthermore, a semi-quantitative and/or qualitative versions could also be used to "screen" for antioxidant power in a sample; for qualitative purposes, a simple visual test of colour change/development could also be used.

DETAILED DESCRIPTION OF THE DRAWINGS

The following examples will help illustrate the invention.

EXAMPLE 1

An Automated Method for Measuring Antioxidant Power: the Ferric Reducing (Antioxidant) Power (FRAP) Assay The method described measures the total antioxidant power of a sample as ferric reducing (antioxidant) power (FRAP value); the representative samples used in this example include human blood plasma and aqueous solutions of individual antioxidants such as ascorbic acid and uric acid. At low pH, when a ferric-tripyridyltriazine ($Fe^{III}$-TPTZ) complex is reduced to the ferrous ($Fe^{II}$) form, and intense blue colour with an absorption maximum at 593 nm develops. The reaction is non-specific, and any half-reaction which has a less positive redox potential, under reaction conditions, than the $Fe^{III}/Fe^{II}$-TPTZ half-reaction, will drive $Fe^{III}$-TPTZ reduction. Test conditions favour reduction of the complex and, thereby, colour development, provided a reductant (antioxidant) is present. Reagent preparation: 300 mmol/l acetate buffer, pH 3.6; 10 mmol/l TPTZ (2,4,6 tripyridyl-s-triazine) in 40 mmol/l HCl; 20 mmol/l $FeCl_3$ $6H_2O$. Working FRAP reagent (redox indicator) was prepared as required by mixing 10 ml acetate buffer, 1.0 ml TPTZ colution and 1.0 ml $FeCl_3$. $6H_2O$ solution.

Samples: aqueous solutions of known $Fe^{II}$ concentration, in the range 100–1,000 $\mu$mol/l, ($FeSO_4 7H_2O$) were used for calibration. Fresh EDTA plasma from 141 adults was chilled and assayed within 5 hours of collection. "Aged plasma" was EDTA plasma that had been pooled and stored at –70° C. for at least two months; aliquots were thawed as required and used as a between-run precision sample. Antioxidants: Solid L-(+) ascorbic acid extra pure crystals, uric acid, solid, albumin, solid (bovine serum albumin, fraction V), bilirubin calibrator solution and TROLOX were used to prepare aqueous antioxidant solutions. DL alpha tocopherol was diluted in ethanol.

Automated FRAP assay: a Cobas Fara centrifugal analyser was used to perform the FRAP assay as follows: 300 $\mu$l freshly prepared FRAP reagent (redox indicator) was warmed to 37° C. and a FRAP reagent blank reading taken (M1) at 593 nm; 10 $\mu$l of sample was then added, along with 30 $\mu$l $H_2O$; final dilution of sample in reaction mixture was, therefore, 1/34. Absorbance (A) readings were taken after 0.5 second and every 15 seconds thereafter during the monitoring period. The change in absorbance ($\Delta A_{593}$nm ) between the final reading selected (4 minutes in this example) and the M1 reading was calculated for each sample and related to $\Delta A_{593}$ nm of a $Fe^{II}$ standard solution tested in parallel.

Figure 1:
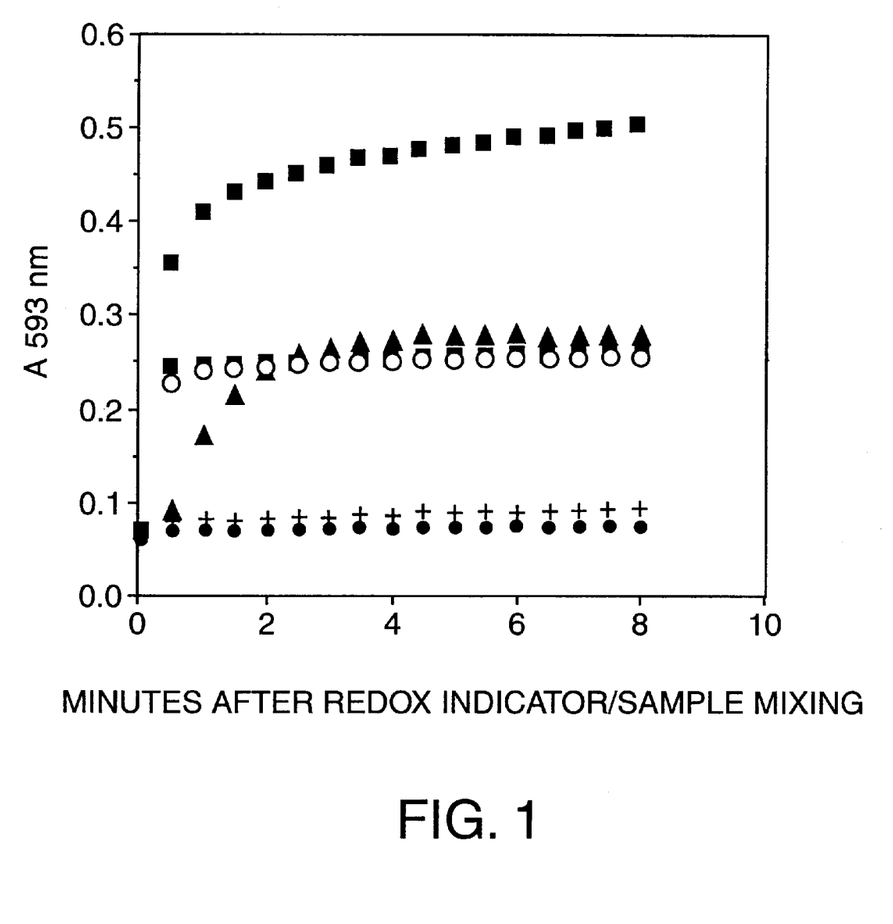
FIG. 1 shows the rate of increase in absorbance at 593 nm for 100 $\mu$mol/l solutions of bilirubin (crossed squares), ascorbic acid (filled squares), uric acid (triangles), alpha tocopherol (open circles) and albumin (plus sign) compared to the monitored absorbance of FRAP reagent only (diamonds), all measured in parallel.

It is seen from the results in FIG. 1 that the reaction with ascorbic acid and alpha tocopherol is very fast, reaching completion in under one minute. The reaction with uric acid reaches an endpoint after 3 minutes. The reactions with the bilirubin preparation and with albumin do not reach an endpoint within the monitoring period, although the reaction of bilirubin is fast in first few seconds and relatively slow by 2 minutes post sample/redox indicator mixing—the continued slow increase being due to the albumin content of the bilirubin calibrator solution used. Reaction of protein (in this case albumin) is slow and slight.

When the test was performed with plasma but with no $Fe^{III}$ added to the reaction mixture, no colour developed. This indicates that there is no detectable free $Fe^{II}$ in EDTA plasma and that there is no detectable agent in normal EDTA plasma that reacts directly with TPTZ to form the blue chromogen. Monitoring FRAP reagent containing TPTZ and $Fe^{III}$, but with no sample addition, showed that no colour developed (FIG. 1, diamonds), indicating negligible spontaneous $Fe^{III}$ reduction in the absence of added antioxidants.

Figure 2:
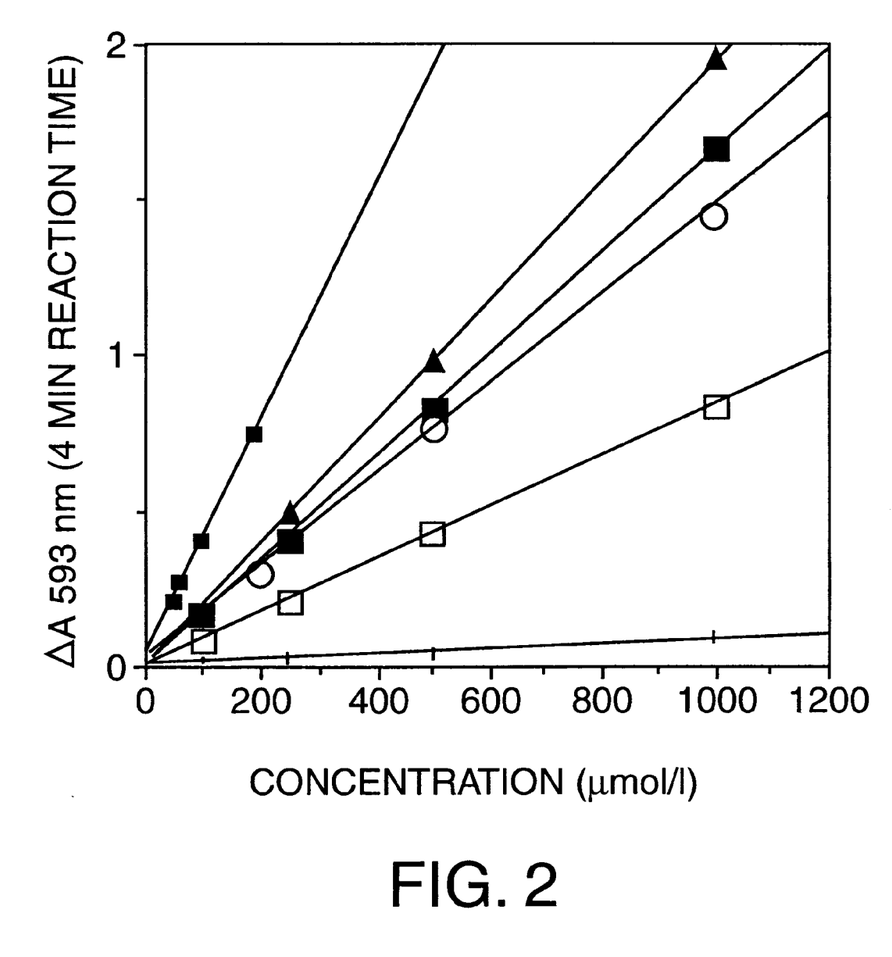
FIG. 2 shows the dose-response lines for solutions of the bilirubin preparation (crossed squares), uric acid (triangles), ascorbic acid (filled squares), alpha tocopherol and TigoloxTM (open circles), $Fe^{II}$ (open squares) and albumin (plus sign); dose response lines of alpha tocopherol and TROLOXTM indistinguishable from each other and are both represented by a common symbol (open circle).

In FIG. 2 it is clearly seen that the linear dose-response obtained for each individual antioxidant implied that the stoichiometric factors, or antioxidant activities, of these antioxidants are not concentration-dependent in this system. However, the relative activities of the individual antioxidants in this system are not all the same. Relative to the reaction of $Fe^{II}$ (representing a one electron exchange reaction and taken as unity), and using the 0–4 minute reaction time window, activities of bilirubin, ascorbic acid, uric acid, alpha tocopherol, TROLOX and albumin were calculated by comparing the amount of any given antioxidant with the amount of $Fe^{II}$ required to give the same absorbance change. Calculated activities of the various antioxidant test are given in Table 1; for alpha tocopherol (and TROLOX), uric acid and ascorbic acid activities were very close to 2.0 at all concentrations tested.

Figure 3:
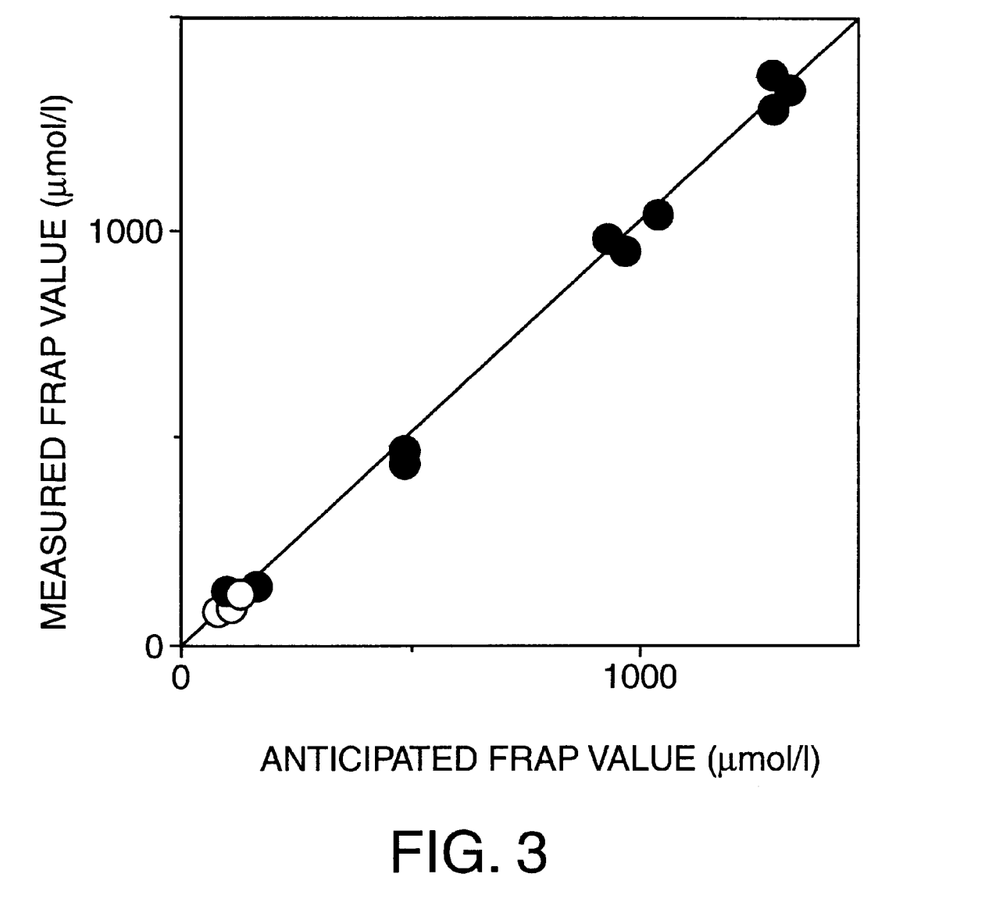
FIG. 3 shows the anticipated FRAP values, by calculation, (x-axis) and the measured FRAP values (y-axis) for known amounts of individual antioxidants that were added to plasma (filled circles) and to water (open circles).
Figure 4:
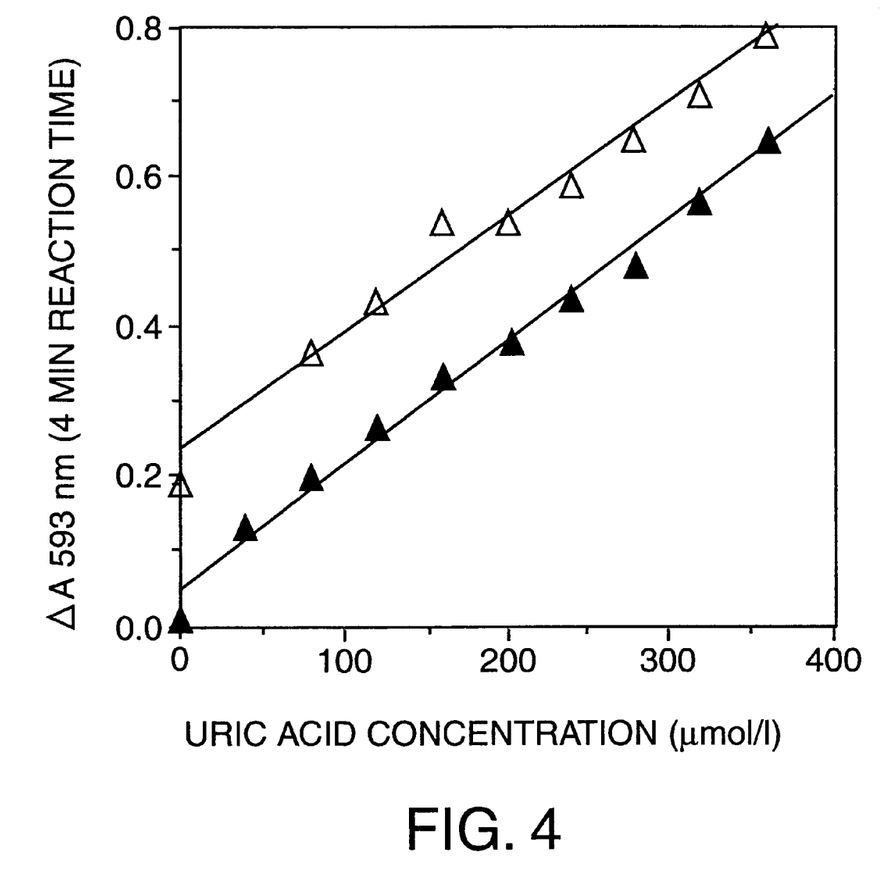
FIG. 4 shows the dose-response relation ship of uric acid, when solutions of uric acid with different concentrations were tested in the presence of 100 $\mu$mol/l ascorbic acid (open triangles ) and without ascorbic acid (closed triangles).

When known amounts of individual antioxidants were mixed and the FRAP value measured, there was good recovery (91–112%). Good agreement was seen between the anticipated, by calculation and measured FRAP values (r=0.990; P<0.001) after known amounts of individual antioxidants were added to plasma (FIG. 3, filled circles) and to water (FIG. 3, open circles). In addition, the FRAP does-response relationship was the same, i.e. parallel lines were obtained, when uric acid solutions of different concentrations were tested with (FIG. 4, open triangles) and without (FIG. 4, filled triangles) the presence of 100 $\mu$mol/l ascorbic acid, and when different concentrations of ascorbic acid were tested with and without 200 $\mu$mol/l uric acid (results not shown). These results all indicate that there is no activity-changing antioxidant interaction in this test system.

Within-run coefficients of variations (CV) were <1.0% at all FRAP values tested (100, 200 and 900 $\mu$mol/l; n=10 in each case). Between-run CV was <3.0% (mean 960 $\mu$mol/l; n=25). Reproducibility of FRAP is, therefore, very high, enhancing the sensitivity of the method.

The mean (median; SD) plasma FRAP value of 141 apparently healthy adults was 1017 (1000; 206) $\mu$mol/l (range 612–1634 $\mu$mol/l). There was a significant correlation between the FRAP values and the plasma uric acid concentrations (r=0.914, P<0.0001; n=141).

To perform the test manually, sample and reagent volumes are simply increased in parallel. Pure, homogeneous solutions of known antioxidants, such as ascorbic acid, can be used as calibrators, but stoichiometric factors must be allowed for.

Some antioxidants may require a longer or shorter reaction time. The pH, temperature and reagent concentrations used by been chosen to given sensitive, linear and highly reproducible response to a range of antioxidants, however, these are not critical, and the test will work over a range of pH, temperature, time and reagent concentration settings.

Other redox reactions and automated system suitable for use in the present inventive methods are known in the art. Numerous types of automated and semi-automated analyzers and instruments are available as are redox indicators that undergo a measurable physicochemical change, such as a colour change, upon reduction by an antioxidant. Such analyzers, instruments and redox indicators are useful in the context of the present invention.

EXAMPLE 2

Measurement of Total Antioxidant Power and Ascorbic acid Concentration in One Simple Biochemical Test The FRASC assay combines the FRAP assay, for antioxidant power, with an enzyme linked spectrophotometric method of measuring ascorbic acid (the EFTSA method). Reagents and equipment useful in the FRAP assay of plasma and in the measurement of plasma ascorbic acid are as described in the EFTSA method, disclosed by Benzie et al., *Analytical Biochemistry* 239,; 70–76 (1996); and Benzie, *Clinical Biochemistry* 29(2): 111–116(1996). Both methods utilize the ability of reductants, i.e., antioxidants, to reduce $Fe^{III}$ to $Fe^{II}$. When complexed to tripyridyltriazine at low pH, reduction of $Fe^{III}$, causes the formation of $Fe^{II}$-TPTZ, which is a blue coloured complex, with a concomitant increase in absorbance at 593 nm.

Ascorbic acid, which reacts almost instantaneously with the $Fe^{III}$-TPTZ complex, is selectively destroyed in the EFTSA assay by the addition of ascorbate oxidase (ascorbate oxidase EC 1.10.3.3) to one of a pair of sample aliquots. $Fe^{III}$ reduction by other antioxidants in plasma is virtually complete by 4 minutes post sample-redox indicator mixing, although there is a small continued increase in absorbance due to the slow reaction of dehydroascorbic acid (DHA), the oxidation product of ascorbic acid, and of protein. The 1 minute post sample-redox indicator mixing absorbance of a sample to which ascorbate oxidase (40 $\mu$l of a 4 $\mu$/ml solution added to 100 $\mu$l sample) was added is subtracted from the absorbance of a matching aliquot to which water (40 $\mu$l added to 100 $\mu$l sample), rather than ascorbate oxidase was added; the difference is due specifically to antioxidant power of ascorbic acid.

Figure 5:
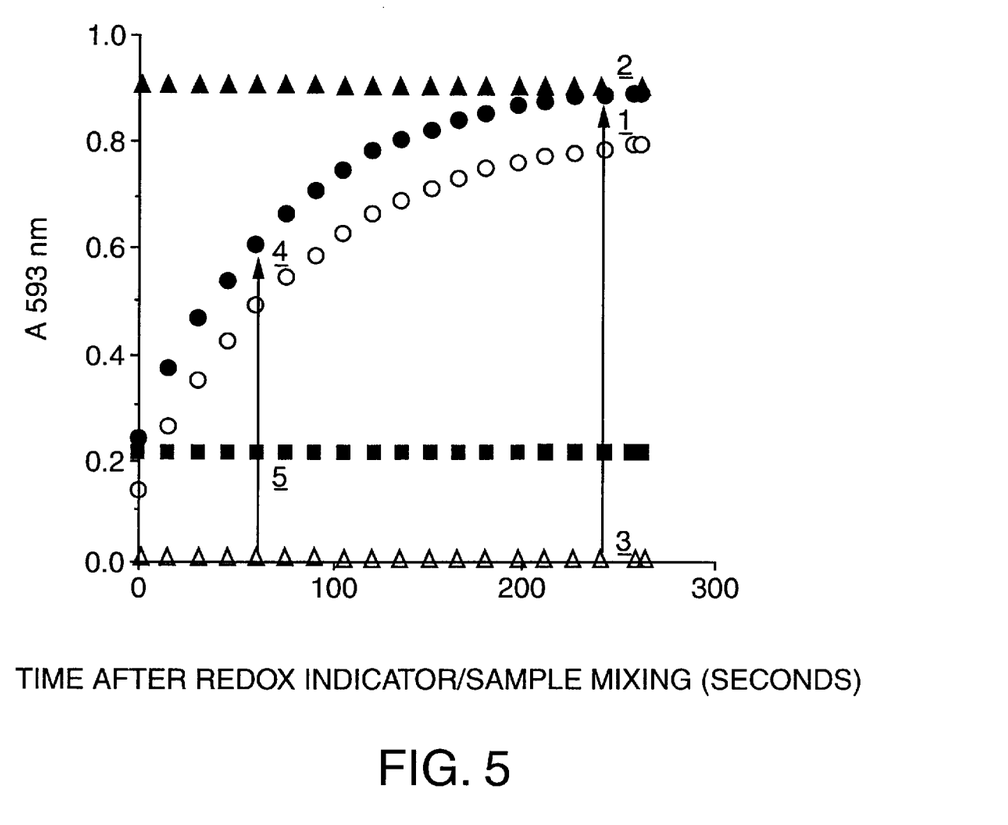
FIG. 5 shows the absorbance change owing to $Fe^{III}$- TPTZ reduction by antioxidants in the sample. Calculation of FRAP value is by taking the 0–4 minute $\Delta A$ for test sample (closed circles, 1) and relating it to the 0–4 minutes $\Delta A$ for the $Fe^{II}$ standard (closed triangles, 2), with a redox indicator (FRAP reagent) blank correction (open triangles, 3) for both. Calculation of ascorbic acid results is by subtracting the 0–1 minute $\Delta A$ reading of the ascorbate oxidase-treated test sample (open circles) from the matching water-treated sample (closed circles, 4); this signal is then related to that given by a standard solution of $Fe^{II}$ (closed triangles) (or ascorbic acid, closed squares, 5) of appropriate concentration.

The 4 minute absorbance change of the aliquot diluted in water is due to the combined reductive activity of all the reacting antioxidants present in the sample, i.e. the 'total antioxidant capacity', or ferric reducing (antioxidant) power; this is referred to as the FRAP value. The 4 minute and 1 minute absorbance changes can be translated into $\mu$mol/l of FRAP and ascorbic acid concentration respectively by comparisons with that of a standard solution of $Fe^{II}$ of appropriate molar concentration, typically 100 and/or 1,000 $\mu$mol/l $FeSO_4 7H_2O$ in water. It should be noted that, since ascorbic acid has a stoichiometric factor of 2.0 in this assay, that 100 $\mu$mol/l $Fe^{II}$ is equivalent to 50 $\mu$mol/l ascorbic acid; freshly prepared ascorbic acid standards may also be used, in which case the FRAP value is twice the ascorbic acid concentration. By monitoring the 0–4 minute absorbance change of paired aliquots of water- and ascorbate oxidase- treated samples run in parallel on a Cobas Fara centrifugal analyser (Roche Diagnostics Ltd. Basel, Switzerland), all the necessary information can be gathered to obtain both the FRAP value and the ascorbic acid concentration of up to 13 pairs of test samples in one run. This concept is represented in FIG. 5, and the Cobas Fara programme used in this representative example is detailed in Table 2.

Working FRASC reagent was prepared as required by mixing 25 ml acetate buffer (300 mmol/l acetate buffer, pH 3.6), 2.5 ml TPTZ solution and 2.5 $FeCl_3 \cdot 6H_2O$ solution.

Calculation of results was performed as follows (see FIG. 5):

Using the water-diluted samples, the FRAP ($\mu$mol/l) value=

0–4 minute $\Delta A_{593\ nm}$ test sample X $[FRAP]_{std}$ ($\mu$mol/l)

0–4 minute $\Delta A_{593\ nm}$ standard

Using the paired water (−ao) and ascorbate oxidase diluted (+ao) samples, the ascorbic acid concentration was calculated as follows:

a) 0–1 minute ascorbic acid related $\Delta A_{593\ nm}$=

(0–1 minute $\Delta A_{593\ nm}$ sample −ao)−(0–1 minute $\Delta A_{593\ nm}$ sample +ao)

b) ascorbic acid concentration ($\mu$mol/l)=[ascorbic acid]$_{std}$ ($\mu$mol/l) X 0–1 minute ascorbic acid related $\Delta A_{593\ nm}$ of test sample 0–1 minute ascorbic acid related $\Delta A_{593\ nm}$ of standard FRASC was performed on the fasting plasma of 130 apparently healthy adults. Data gathered were used to provide baseline reference values for total 'antioxidant' (reducing) capacity (as $\mu$mol/l FRAP) and ascorbic acid.

EXAMPLE 3

Experiment to investigate the effect of dilution on the FRAP values:

One aspect of importance in the evaluation of FRASC was to investigate possible dilution effects on the FRAP values obtained on plasma samples. Any dilution effect on antioxidant efficiencies, or stoichiometric factors, would mean that prediluted samples would not be suitable for the measurement of the total ferric reducing ability of plasma. In addition, the effect of the pre-dilution step (required for the measurement of ascorbic acid) on the precision of FRAP results was investigated.

1 EDTA plasma was prediluted in distilled water, and the FRAP value of each dilution measured in duplicate in a single run.

2 the FRAP values of 25 EDTA plasma samples were measured with and without predilution in water (100 $\mu$l sample) plus 40 $\mu$l of water, the predilution required by the EFTSA method of ascorbic acid concentration). All samples were measured twice, in separate runs, FRAP values ($\mu$mol/l) were obtained with reference to a $Fe^{II}$ standard solution run in parallel and treated identically to the samples in each case, i.e. prediluted or non-prediluted in water as appropriate.

Within, and between, run precision of the FRAP assay was assessed by repeated measurement of pooled, aged plasma with and without a spike of ascorbic acid (prepared from solid L−(+) ascorbic acid extra pure crystals). Aged plasma refers to EDTA plasma stored at −70° C. for at least 3 months; as ascorbic acid is unstable in plasma ex vivo, even at very low temperatures, aged plasma contains no native ascorbic acid. Precision of the ascorbic acid assay was by repeated measurement of fresh aqueous ascorbic acid solutions and fresh plasma (within-run) and freshly prepared ascorbic acid-spiked aged plasma (between-run).

Fresh EDTA plasma samples used were from 130 apparently healthy, fasting, adults from whom informed consent had been obtained. Fasting blood samples, from the antecubital vein, were kept chilled and in the dark until separation of plasma, which was within 3 hours of sample collection; FRASC measurements were performed immediately after separation.

RESULTS

The FRASC procedure is simple and straightforward, high precision is maintained, and predilution of samples does not cause an appreciable change in the relative reductive ability of plasma, i.e. there is no significant difference in the total antioxidant (reducing) power, as FRAP, between the prediluted and non prediluted samples when the dilution factor is taken into account.

Figure 6:
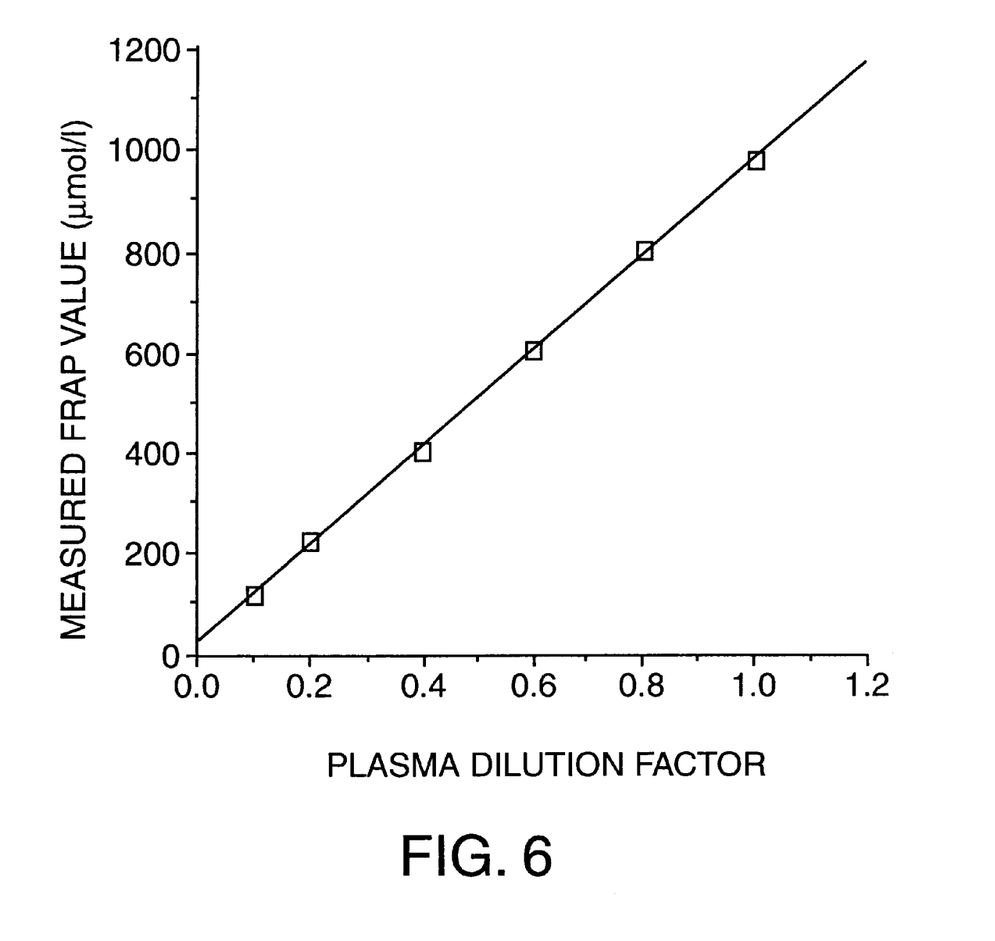
FIG. 6 shows the effect of dilution of a heterogenous solution (in this case blood plasma) on measured FRAP values. Results show excellent agreement between expect and measured FRAP values, indicating no loss of relative reductive activity of reacting antioxidants on a unit for unit basis.
Figure 7:
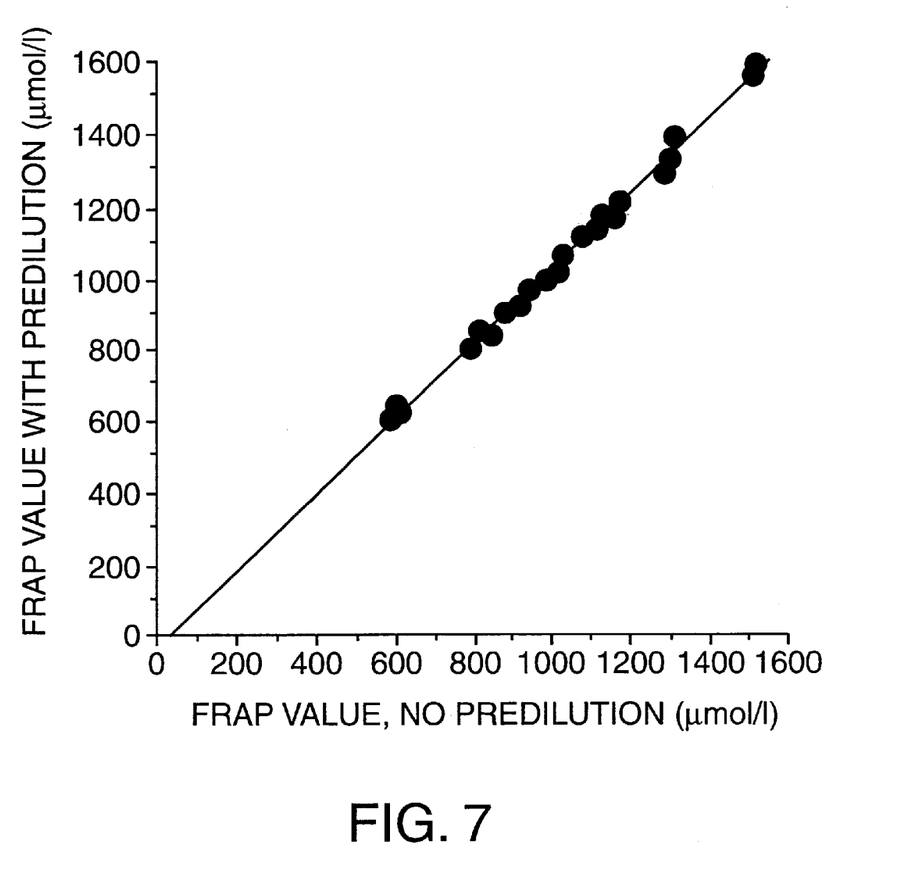
FIG. 7 shows the relationship between measured FRAP values on EDTA plasma with no predilution step and after predilution of 100 $\mu$l plasma and 40 $\mu$l water. Excellent agreement was seen (r=0.998; y=1.03x–23), showing no net loss or gain of reductive activity with dilution.

FIG. 6 shows the FRAP values obtained on plasma prediluted in water by up to a factor of 10. There was excellent agreement between the dilution factor and the measured FRAP value (r=1.00), indicating that there is no dilution effect on the reductive capacity of antioxidants in plasma, i.e. their stoichiometric factors are constant in the FRAP assay. FIG. 7 shows the scatter plot between FRAP values of 25 plasma samples, each measured twice in separate runs, with and without predilution. Again, very good agreement is seen (r=0.998; P<0.0001). Mean (SD) FRAP values, in $\mu$mol/l, of the neat and prediluted samples were 998 (217) and 1,010 (225). When analysed using a paired Student's t-test, the differences between the paired results were statistically significant (P<0.001); however, in both absolute and relative terms the difference is small, averaging 11 $\mu$mol/l (1%). It is suggested, therefore, that this difference is not clinically significant.

FRAP within, and between, run CVs were, respectively, <1% and <3% at 900 and 1800 $\mu$mol/l, n≥10 in each case. Ascorbic acid within- and between-run CVs were <5% at 25, 50, 100 and 440 $\mu$mol/l, n≥10 in each case. Precision of FRASC is, therefore, acceptable for both parameters.

Table 3 shows the FRAP and ascorbic acid concentrations obtained, using FRASC, on the fasting plasma of 130 apparently healthy Chinese adults (66 men, 64 women) aged 21–74 years. From these results it can be seen that ascorbic acid, with a stoichiometric factor of 2.0, contributes around 10–15% of the total antioxidant capacity of fasting plasma. It can also be seen that men had FRAP values around 140 $\mu$mol/l higher (P <0.0001) than those of women. This is likely to be due to the higher uric acid concentrations of men.

TABLE 1

Relative Activity of Individual Plasma Antioxidants and Their Estimated Contributions to Total FRAP Value

| Plasma Antioxidant | Relative Activity (Measured Range) | Expected Fasting Plasma Concentration $\mu$mol/t | Estimated % Contribution to Total FRAP of Plasma |
|---|---|---|---|
| Ascorbic Acid | 2.0 (1.9–2.1) | 30–100 | 15% |
| Alpha Tocopherol | 2.0 (1.7–2.1) | 15–40 | 5% |
| Uric Acid | 2.0 (2.0–2.4) | 150–450 | 60% |

TABLE 1-continued

Relative Activity of Individual Plasma Antioxidants
and Their Estimated Contributions to Total FRAP Value

| Plasma Antioxidant | Relative Activity (Measured Range) | Expected Fasting Plasma Concentration μmol/t | Estimated % Contribution to Total FRAP of Plasma |
|---|---|---|---|
| Bilirubin | 4.0 (4.2–4.6) | <20 | 5% |
| Protein | 0.10 (0.1–0.15) | 800–1,100 | 10% |
| Others | — | — | 5% |

*based on albumin-corrected readings

TABLE 2

COBAS FARA TEST PROGRAMME FOR
PLASMA TOTAL 'ANTIOXIDANT'
(REDUCING) CAPACITY (FRAP VALUE)
AND ASCORBIC ACID CONCENTRATION
BY FRASC

| | |
|---|---|
| Measurement mode | Abs |
| Reaction mode | R1-I-S-A |
| Reagent blank | reag/dil |
| Wavelength | 593 nm |
| Temperature | 37° C. |
| R1 | 300 μl |
| M1 | 1.0 s |
| Sample volume | 10 μl |
| Diluent name | H$_2$O |
| Volume | 30 μ |
| Readings: | |
| first | 0.5 s |
| number | 17 |
| interval | 15 s |
| Reaction direction | increase |
| Number of steps | 1 |
| Calculation | endpoint |
| first | M1 |
| last | 17 (i.e. 4 m) for FRAP |
| | 5 (i.e. 1 m) for ascorbic acid |

TABLE 3

FRAP VALUES AND ASCORBIC ACID CONCENTRATIONS
(MEAN; MEDIAN; SD) USING FRASC, OF FRESH EDTA PLASMA
FROM HEALTHY SUBJECTS

| | All (n = 130) | Men (n = 66) | Women (n = 64) |
|---|---|---|---|
| Age (years) | 43;43;16.4 | 42;42;16.3 | 43;44;16.6 |
| FRAP (μmol/L) | 1018;1004;198 | 1086;1077;189 | 948*;927;183 |
| Ascorbic acid (μmol/L) | 51;48;17.9 | 49;48;13.8 | 52;50;21.3 |

*significantly different from corresponding value in men: $P < 0.0001$

What is claimed is:

1. A method of assaying the antioxidant capacity of a given antioxidant present in a composition comprising one or more antioxidants selected from the group consisting of thiol group containing proteins, glutathione, cysteine, flavonoids, and vitamin E, said method comprising:
   (i) contacting a first sample of said composition with an oxidant to cause an electron transfer reaction that results in a first change in absorbance of electromagnetic radiation;
   (ii) deactivating the antioxidant ability of said given antioxidant in a second sample of said composition to obtain a partially deactivated sample;
   (iii) contacting said partially deactivated sample with an oxidant to cause an electron transfer reaction that results in a second change in absorbance of electromagnetic radiation; and
   (iv) comparing said first and second changes in absorbance of electromagnetic radiation.

2. The method of claim 1, wherein the oxidant is a redox indicator.

3. The method of claim 2, wherein the redox indicator is a $Fe^{III}$ complex.

4. A method of assaying the total antioxidant capacity and the amount of a given antioxidant in a composition comprising more than one antioxidant, said method comprising:
(i) contacting a first sample of said composition with a redox indicator selected from the group consisting of a ferric tripyridyl triazine complex, ferric dipyridyl triazine complex, ferrozine, and ferric bathophenanthroline to cause an electron transfer reaction that results in a first change in absorbance of electromagnetic radiation; (ii) deactivating said given antioxidant in a second sample of said composition to obtain a partially deactivated sample; (iii) contacting said partially deactivated sample with a redox indicator selected from the group consisting of a ferric tripyridyl triazine complex, ferric dipyridyl triazine complex, ferrozine, and ferric bathophenanthroline to cause an electron transfer reaction that results in a second change in absorbance of electromagnetic radiation; (iv) measuring the first and second changes in absorbance of electromagnetic radiation relative to a standard; and (v) determining the total antioxidant capacity of the composition and the amount of the given antioxidant from said first and second changes in absorbance of electromagnetic radiation wherein said deactivation is carried out by a process selected from the group consisting of filtration, precipitation, chromatography, and centrifugation.

5. A method of assaying the antioxidant capacity of flavonoids present in a composition comprising flavonoids and one or more antioxidants selected from the group consisting of thiol group containing proteins, glutathione, cysteine, and vitamin E, said method comprising: (i) contacting a first sample of said composition with an oxidant to cause an electron transfer reaction that results in a first change in absorbance of electromagnetic radiation; (ii) deactivating the antioxidant ability of said flavonoids in a second sample of said composition of obtain a partially deactivated sample; (iii) contacting said partially deactivated sample with an oxidant to cause an electron transfer reaction that results in a second change in absorbance of electromagnetic radiation; and (iv) comparing said first and second changes in absorbance of electromagnetic radiation.

6. The method of claim 5, wherein the oxidant is a redox indicator.

7. The method of claim 6, wherein the redox indicator is a $Fe^{III}$ complex.

8. The method of claim 7, wherein the $Fe^{III}$ complex is selected from the group consisting of ferric tripyridyltriazine complex, ferric dipyridyl triazine complex, ferrozine, and ferric bathophenanthroline.

9. The method of claim 5, wherein said deactivation is carried out by an enzyme.

10. The method of claim 5, wherein said deactivation is carried out by a process selected from the group consisting of filtration, precipitation, chromatography, and centrifugation.

11. The method of claim 5, wherein said deactivation is reversible.

12. The method of claim 5, wherein said vitamin E is selected from the group consisting of alpha tocopherol, beta tocopherol, gamma tocopherol, delta tocopherol, tocotrienols, and 6-hydroxy,2,5,7,8-tetramethyl chroman-2-carboxylic acid.

* * * * *